United States Patent
Malchow et al.

(10) Patent No.: US 8,702,887 B2
(45) Date of Patent: Apr. 22, 2014

(54) APPARATUS FOR AND METHOD OF APPLYING RIBBON IN A NONLINEAR PATTERN TO A WEB

(75) Inventors: Greg Malchow, Oshkosh, WI (US); Paul Weber, Menasha, WI (US); Jesse Sorenson, Neenah, WI (US); Caleb Ihrig, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 352 days.

(21) Appl. No.: 12/971,942

(22) Filed: Dec. 17, 2010

(65) Prior Publication Data

US 2012/0152440 A1  Jun. 21, 2012

(51) Int. Cl.
*A61F 13/15* (2006.01)
*B32B 37/00* (2006.01)

(52) U.S. Cl.
USPC ........... 156/161; 156/163; 156/164; 156/229; 156/494; 156/495; 156/496

(58) Field of Classification Search
USPC .......... 156/161, 160, 163, 164, 229, 494–496
See application file for complete search history.

(56) References Cited

U.S. PATENT DOCUMENTS

| | | | |
|---|---|---|---|
| 3,231,970 A * | 2/1966 | Wardell | 29/414 |
| 4,041,203 A | 8/1977 | Brock et al. | |
| 4,281,619 A | 8/1981 | Frick et al. | |
| 4,293,367 A | 10/1981 | Klasek et al. | |
| 4,617,082 A | 10/1986 | Oshefsky et al. | |
| 4,675,068 A | 6/1987 | Lundmark | |
| 4,915,767 A * | 4/1990 | Rajala et al. | 156/440 |
| 4,917,746 A * | 4/1990 | Kons et al. | 156/164 |
| 4,987,940 A | 1/1991 | Straub et al. | |
| 4,995,928 A | 2/1991 | Sabee | |
| 5,221,390 A | 6/1993 | Persson et al. | |
| 5,236,539 A | 8/1993 | Rogberg et al. | |
| 5,275,676 A | 1/1994 | Rooyakkers et al. | |
| 5,389,173 A * | 2/1995 | Merkatoris et al. | 156/164 |
| 5,525,175 A | 6/1996 | Blenke et al. | |
| 5,660,657 A | 8/1997 | Rajala et al. | |
| 5,779,689 A | 7/1998 | Pfeifer et al. | |
| 6,217,690 B1 | 4/2001 | Rajala et al. | |
| 6,287,409 B1 | 9/2001 | Stephany | |
| 6,378,750 B1 | 4/2002 | Disano et al. | |
| 6,432,242 B1 | 8/2002 | Nielsen et al. | |

(Continued)

FOREIGN PATENT DOCUMENTS

| | | |
|---|---|---|
| EP | 1842516 A1 | 10/2007 |
| JP | 7255777 A | 1/1995 |
| WO | 9623477 A2 | 8/1996 |
| WO | 2004078083 A1 | 2/2004 |

OTHER PUBLICATIONS

International Search Report and Written Opinion for PCT/IB2011/054984 dated Jul. 30, 2012; 9 pages.

*Primary Examiner* — Jeff Aftergut
(74) *Attorney, Agent, or Firm* — Armstrong Teasdale LLP

(57) ABSTRACT

Apparatus for applying ribbon in a nonlinear pattern to a web includes a guide assembly having a roller adapted to guide the ribbon onto the web as the web is moving in a first direction. A reciprocating device is provided to move at least the roller of the guide assembly back and forth along an axis of motion. The axis of motion is other than parallel to the first direction.

25 Claims, 10 Drawing Sheets

(56) References Cited

U.S. PATENT DOCUMENTS

| | | |
|---|---|---|
| 6,589,149 B1 | 7/2003 | VanEperen et al. |
| 6,890,630 B2 | 5/2005 | Franklin et al. |
| 6,895,649 B2 * | 5/2005 | Kojo et al. ................ 29/407.01 |
| 7,048,991 B2 | 5/2006 | Franklin et al. |
| 7,273,476 B2 * | 9/2007 | Mueller et al. ........... 604/385.24 |
| 2002/0023706 A1 | 2/2002 | Vogt et al. |
| 2005/0000628 A1 | 1/2005 | Norrby |
| 2005/0148985 A1 * | 7/2005 | Bronk et al. ................ 604/387 |
| 2005/0258199 A1 * | 11/2005 | Honer et al. .................... 223/66 |
| 2008/0105384 A1 | 5/2008 | Eckstein |
| 2009/0020211 A1 | 1/2009 | Andrews et al. |
| 2009/0157036 A1 | 6/2009 | Ponomarenko et al. |

* cited by examiner

APPARATUS FOR AND METHOD OF APPLYING RIBBON IN A NONLINEAR PATTERN TO A WEB

BACKGROUND

The field of the invention relates generally to apparatus for and methods of applying ribbon to a web and more particularly to apparatus for and method of applying ribbon in a nonlinear pattern to a moving web.

Absorbent articles, such as disposable diapers, training pants, adult incontinence articles and the like, generally include several different components that are bonded together. Typical absorbent articles include a bodyside liner, an outer cover, and an absorbent core disposed between the liner and outer cover. Besides the liner, outer cover, and absorbent core, typical absorbent articles also include a number of discrete components, e.g., fasteners, waist elastics, leg elastics. These discrete components of the article are often bonded to the bodyside liner and/or the outer cover. For example, it is known to adhesively bond leg elastics in a curved pattern to a continuous web of outer cover material or bodyside liner material.

However, known techniques for applying leg elastics to a web moving at high line speeds are often limited in the amount of displacement (e.g., the amount of amplitude in a curved pattern) that can be achieved. Thus, leg elastics in known absorbent articles produced at high line speeds are often straight or relatively straight. The leakage protection and the aesthetic appearance of known absorbent articles can be improved, however, by incorporating leg elastics with significant curvature along their lengths.

Known efforts to place leg elastics with significant amounts of displacement (i.e., curvature) onto a web at high line speeds have been unsuccessful. These efforts have resulted in leg elastics being placed off target. Moreover, the deviation of the applied leg elastics from the target was not always the same.

As a result, it is desirable to provide an apparatus and method for accurately applying a ribbon in a nonlinear manner to a web moving at high line speeds.

BRIEF DESCRIPTION

In one aspect, apparatus for applying ribbon in a nonlinear pattern to a web generally comprises a guide assembly including a roller adapted to guide the ribbon onto the web as the web is moving in a first direction. A reciprocating device is provided for moving at least the roller of the guide assembly back and forth along an axis of motion. The axis of motion is other than parallel to the first direction.

In another aspect, apparatus for applying ribbon in a nonlinear pattern to a web generally comprises a guide assembly including a roller adapted to guide the ribbon onto the web as the web is moving in a first direction. A slider-crank assembly is operatively connected to guide assembly to impart reciprocating motion on at least the roller of the guide assembly so that the roller can be moved back and forth relative to the web as it guides the ribbon onto the web.

In yet another aspect, a method of applying a ribbon to a web generally comprises feeding a web at a high line speed in a machine direction and guiding a ribbon to the web using a guide roller. The ribbon is guided by the guide roller in a nonlinear pattern such that at least a portion of the ribbon has a radius of curvature between about 3 inches and about 10 inches.

BRIEF DESCRIPTION OF THE DRAWINGS

Corresponding reference characters indicate corresponding parts throughout the drawings.

DETAILED DESCRIPTION OF THE DRAWINGS

Figure 1:
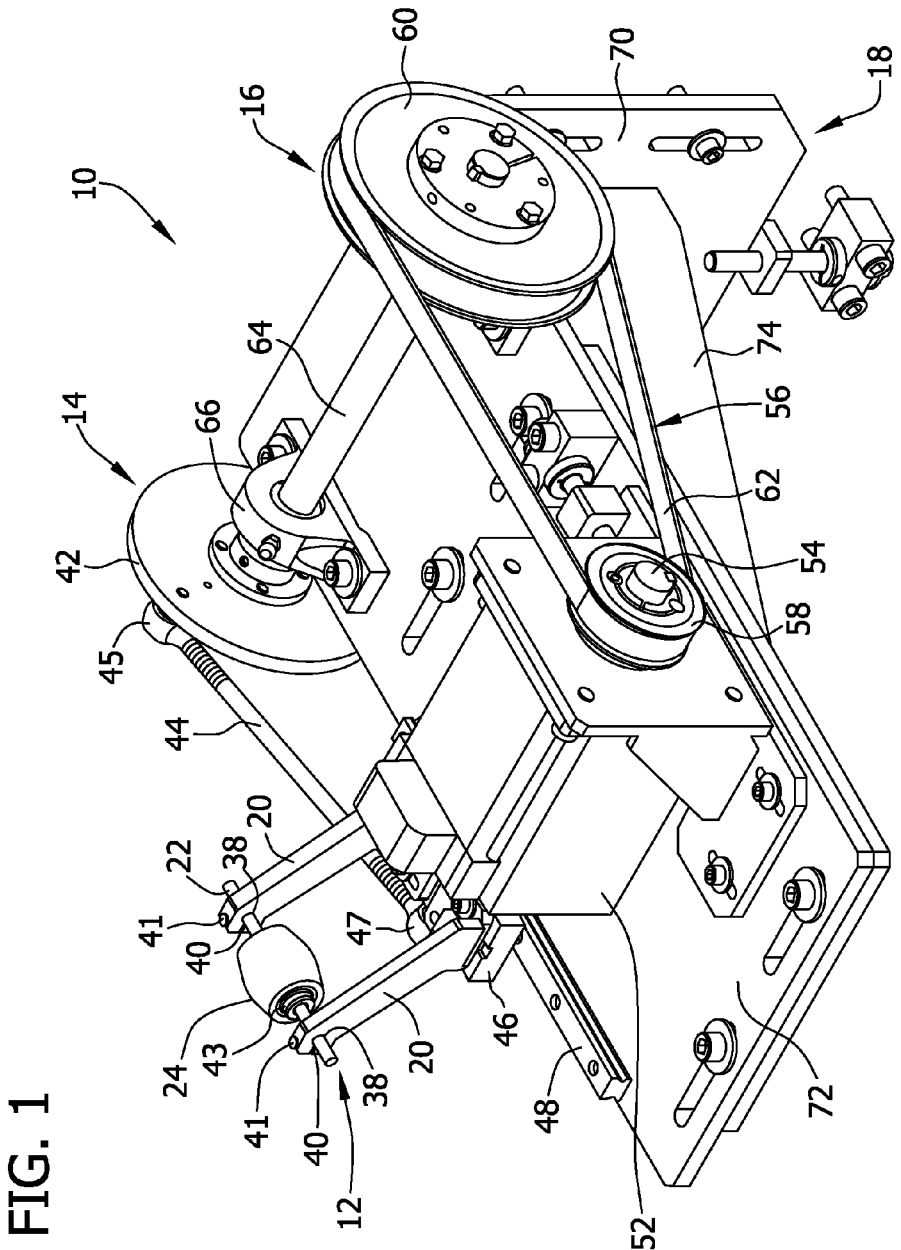
FIG. 1 is a perspective of one embodiment of an apparatus for adhesively bonding ribbon in a nonlinear pattern to a web.

FIGS. 1-5 illustrate one suitable embodiment of an apparatus, indicated generally at 10, for applying ribbon in a nonlinear pattern to a web while the web is moving at a high line speed. The illustrated apparatus 10 comprises a guide assembly 12, a slider-crank assembly 14, a drive assembly 16, and a platform assembly 18. The guide assembly, the slider-crank assembly, the drive assembly, and the platform assembly are indicated generally by their respective reference numbers in the accompanying Figures.

Figure 2:
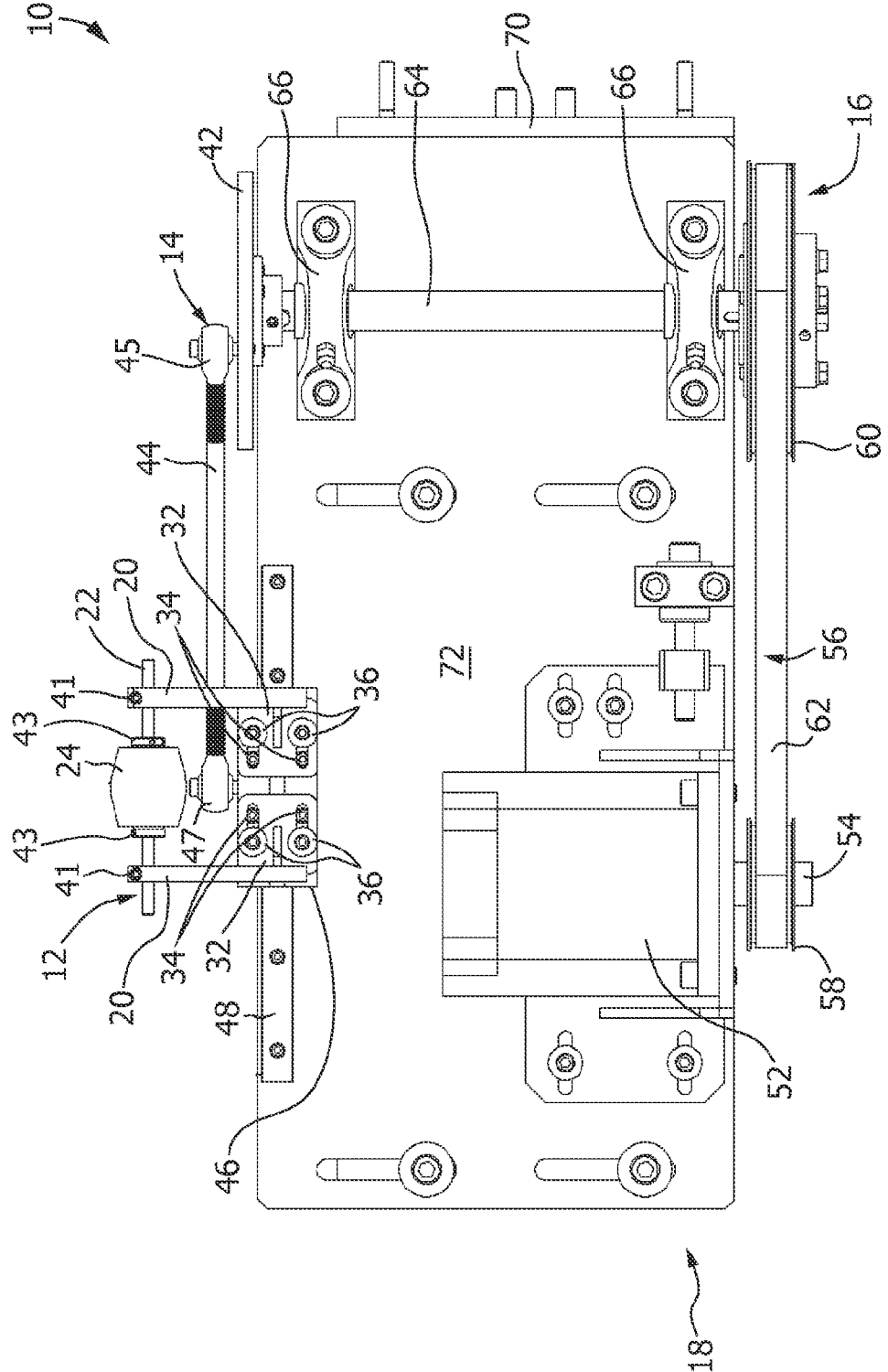
FIG. 2 is a top plan view of the apparatus.
Figure 3:
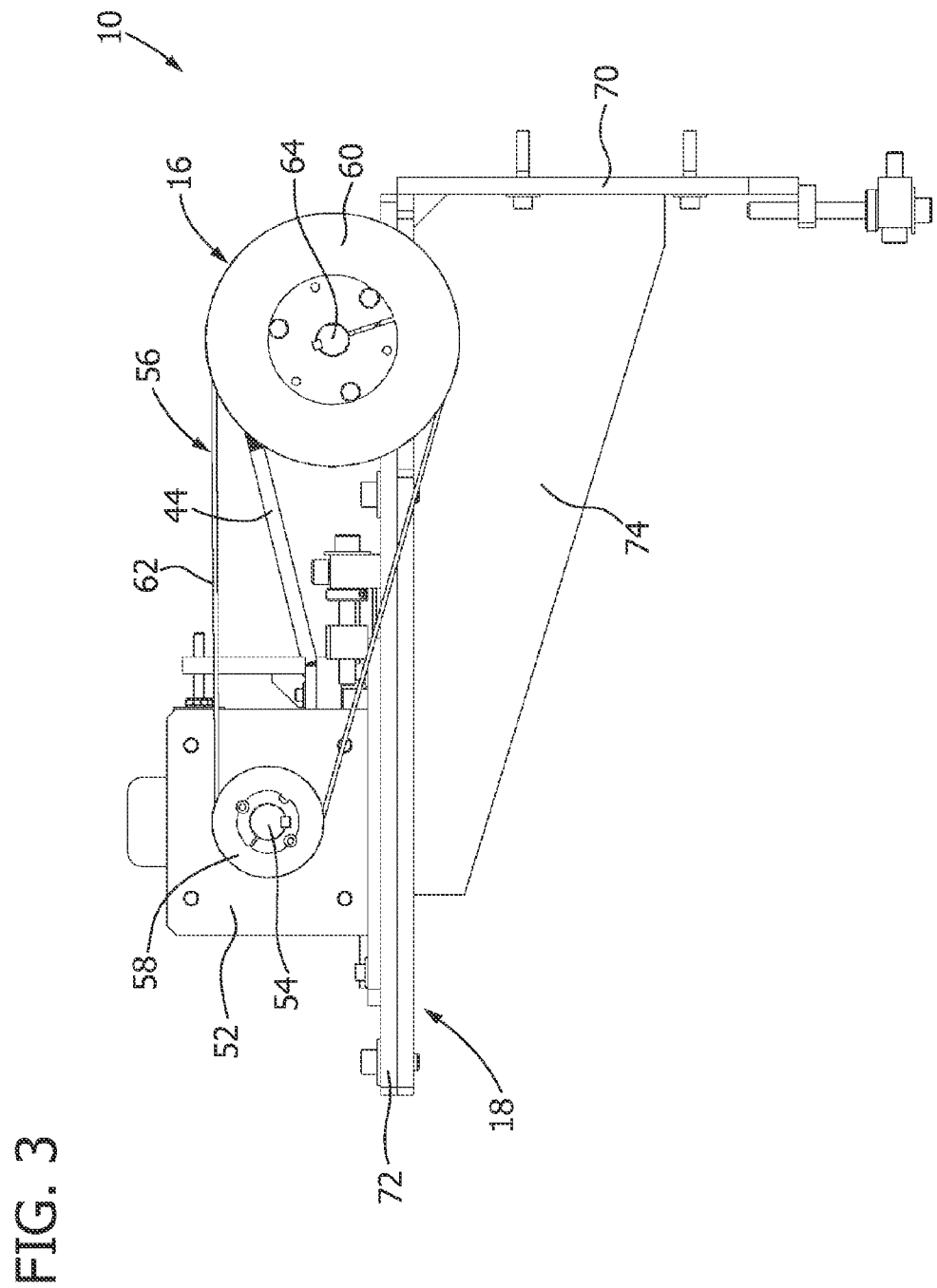
FIG. 3 is a right side elevation of the apparatus.
Figure 5:
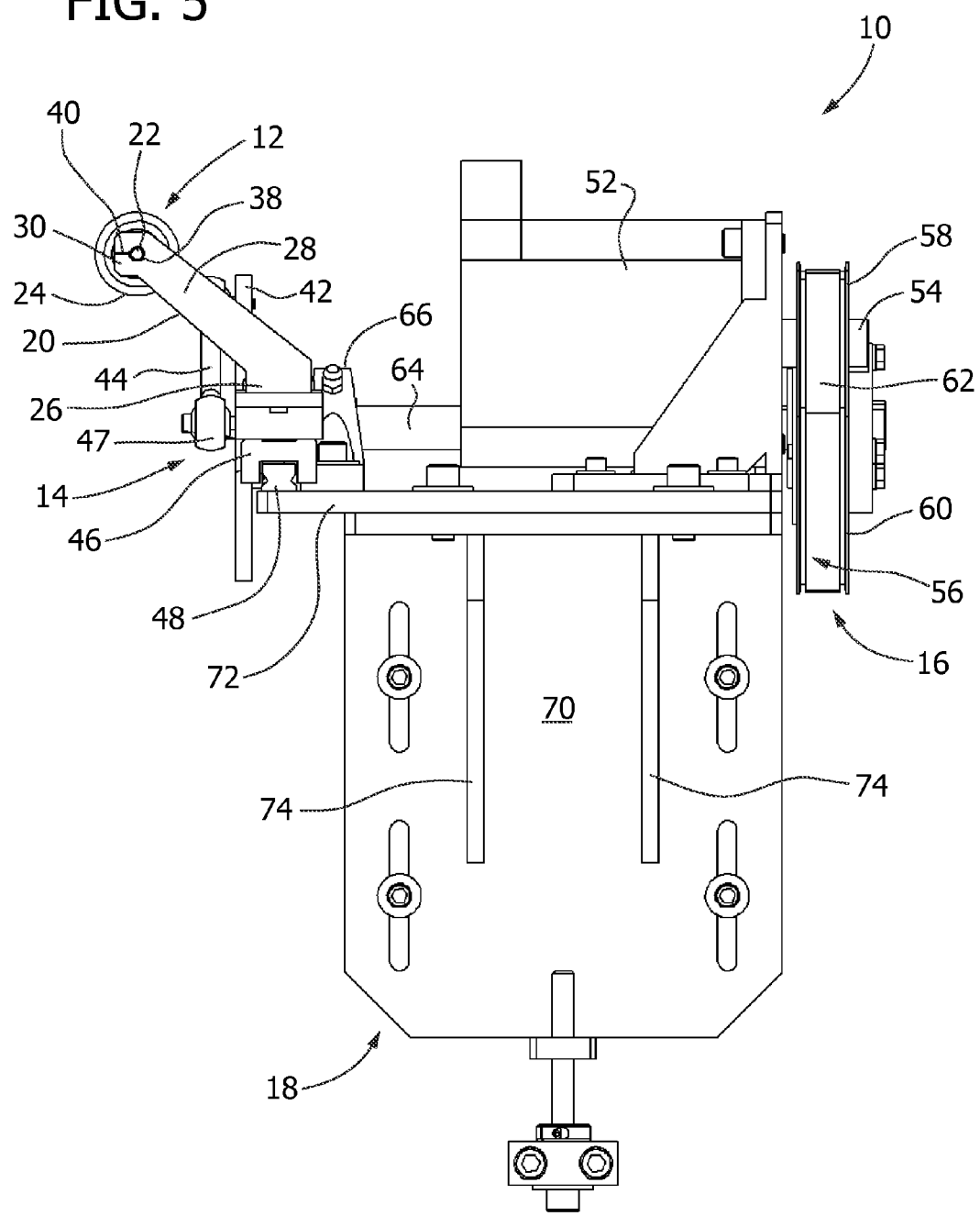
FIG. 5 is a bottom plan view of the apparatus.

The guide assembly 12 includes a pair of spaced-apart support arms 20, a shaft 22 extending between arms, and a roller 24 rotatably mounted on the shaft. Each of the arms 20 of the guide assembly 12 includes a base 26 mounted to the slider-crank assembly 14, a intermediate portion 28 extending upward from the base, and a free end 30 extending outward from the intermediate portion (FIG. 5). With reference now to FIG. 2, each of the bases 26 includes a mounting plate having a pair of elongate slots 34. A bolt 36 is received in each of the slots 34 for securing the mounting plate 32 and thereby the respective arm 20 to the slider-crank assembly 14. It is understood that the arms 20 can be mounted to the slider-crank in other ways (e.g., welded).

In the illustrated embodiment, the spacing between the arms 20 can be selectively adjusted (increased or decreased) by loosening the bolts 36 and sliding the arms in the desired direction relative to the bolts. Once the desired relative positioning of the arms 20 is achieved, the bolts 36 can be retightened to secure the bolts, which extend through the slots 34 in the mounting plants 32 of the arms 20, to the slider-crank assembly 14. It is contemplated that the relative positioning of the arms 20 can be fixed or adjustable in other ways.

As seen in FIG. 5, the intermediate portion 28 of each of the arms 20 is angled relative to the base 26. In the illustrated embodiment, for example, the intermediate portion 28 is angled approximately 45 degrees relative to the base 26. As also seen in FIG. 5, the free end 30 of each of the arms 20 extend outward at an angle relative to the intermediate portion 28. The free ends 30 are angled at approximately 45 degrees relative to the intermediate portion 28. It is understood, however, that the intermediate portions 28 and the free ends 30 of the arms 20 can have different orientations than those provided herein.

With reference still to FIG. 5, each of the free ends 30 of the arms 20 includes an aperture 38 for receiving the shaft 22 and a cut line 40 extending between an outer edge of the free end and the aperture 38. The cut line 40 increases the flexibility of the arm and thereby aids in the insertion and removal of the shaft 22 into and out of the apertures 38. A fastener 41 is provided in each of the free ends 30 to secure the shaft 22 within the arms 20 (FIG. 2). The fasteners 41 extend through the cut line 40 to thereby inhibit the flexing of the arm 20 when the fastener is secured in place. It is contemplated that the cut line 40 and fastener 41 can be omitted from each of the arms 20.

With reference to FIGS. 1 and 2, the shaft 22 comprises an elongate, cylindrical rod extending through the aperture 38 in each of the arms 20. The shaft 22, in the illustrated embodiment, is supported by the arms 20 in a fixed position. That is, the shaft 22 cannot rotate relative to the arms 20. It is contemplated, however, that in other embodiments of the apparatus 10 the shaft 22 may rotate relative to the arms 20.

The shaft 22 has a length suitable for allowing the arms 20 to be moved further apart form each other. That is, the arms 20 can be spread apart without having to replace the shaft 22 with a longer one. Thus, in the illustrated embodiment, the shaft 22 extends outward beyond the arms 20 but it is understood that the ends of the shaft can be flush with arms or terminate within the openings 38 in the arms.

With reference still to FIGS. 1 and 2, the illustrated roller 24, which is rotatably mounted on the shaft 22, is a truncated prolate spheroid (i.e., shaped like a truncated football). As a result, the roller 24 tapers from its transverse center toward each of its edges. It is understood, however, that the roller 24 can have different shapes, e.g., cylindrical, spool-shaped, hour-glass shaped or other suitable shapes and remain within the scope of this invention.

The roller 24 includes a longitudinal passage (not clearly shown) for allowing the shaft 22 to pass through the roller. A pair of bearings 43 is disposed between the roller 24 and the shaft 22 to facilitate rotation of the roller relative to the shaft. It is contemplated that in an embodiment where the shaft 22 can rotate relative to the arms 20, the roller 24 and shaft can be formed as a single-piece.

Figure 4:
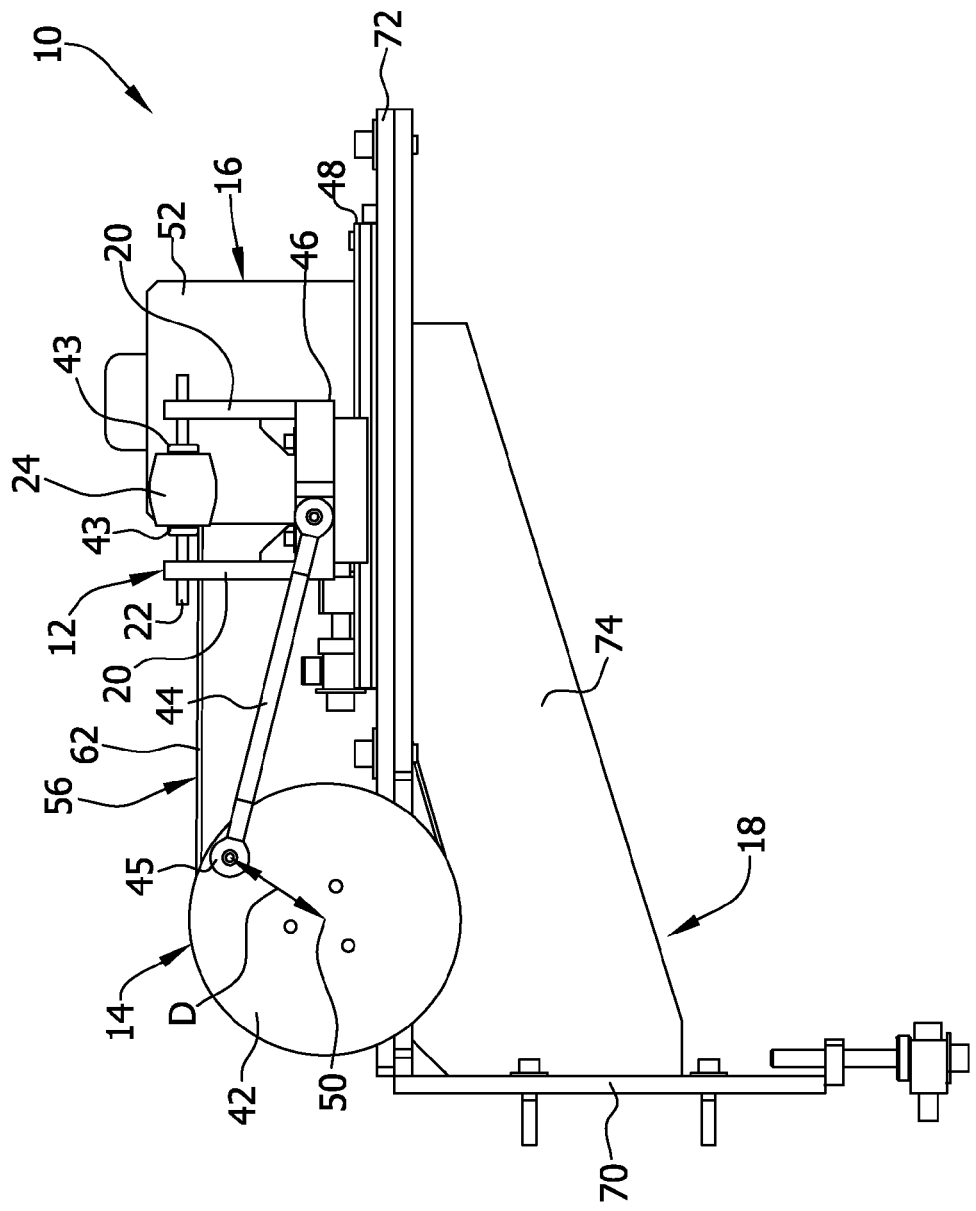
FIG. 4 is left side elevation of the apparatus.

As seen in FIG. 4, the slider-crank assembly 14 (broadly, a "reciprocating device") includes a wheel 42, a rod 44 secured at one end 45 to the wheel, and a slider 46 secured to the opposite end 47 of the rod. Rotation of the wheel 42 causes the end 45 of the rod 44 attached thereto to rotate. Rotation of the rod 44 causes the slider 46 to reciprocate (e.g., slide) back and forth along a rail 48. Thus, the slider-crank assembly 14 converts rotary motion (from the drive assembly 16) into reciprocating motion that is transferred to the guide assembly 12. In the illustrated embodiment, the wheel 42 is generally circular in shape. However, it is contemplated that the wheel 42 can be eccentric (e.g. elliptical) or any other suitable shape. The operation of the slider-crank assembly and its interrelation with the drive assembly 16 and the guide assembly 12 is described in more detail below.

With reference still to FIG. 4, the rod 44 in the illustrated embodiment is secured (e.g., bolted) to the wheel 42 at a location generally adjacent an outer edge of the wheel. The amount of travel imparted on the rod 44 by the wheel 42 is a function of the distance D between the rod and a center 50 of the wheel. The larger the distance D between the center 50 and an end 45 of the rod 44 attached to the wheel, the greater the amount of reciprocating travel that will be imparted on the slider 46. In one suitable embodiment, the distance D can be selectively changed by moving the location at which the end 45 of the rod 44 is attached to the wheel 42.

In the illustrated embodiment, the slider-crank assembly 14 is provided to impart reciprocating motion onto the guide assembly 12. It is contemplated that in other embodiments, the guide assembly can be reciprocated using other devices, such as, a servo motor, cam box, bar linkage, and reciprocating screw.

With reference again to FIG. 1, the drive assembly 16 includes a motor 52, a drive shaft 54 extending outward from the motor, and a belt and pulley subassembly, indicated generally at 56, operatively connected to the drive shaft. In the illustrated embodiment, the motor 52 is capable of rotating the drive shaft 54 at variable speeds and in both the clockwise and counterclockwise directions. It is contemplated that in other embodiments, the motor 52 can be capable of rotating the drive shaft 54 at a single speed and/or in only a single direction.

As seen in FIG. 1, the belt and pulley subassembly 56 includes a first pulley 58 mounted on the drive shaft 54 for conjoint rotation therewith and a second pulley 60 disposed in spaced relation from the first pulley. A belt 62 of the belt and pulley subassembly 56 operatively connects the first and second pulleys 58, 60. Thus, rotational motion imparted on the first pulley 58 by the motor 52 via the drive shaft 54 is transferred to the second pulley 60 by the belt 62.

In the illustrated embodiment, the second pulley 60 has a substantially larger diameter than the first pulley 58. It is understood, however, that the relative diameters between the first and second pulleys 58, 60 can be different than those illustrated herein. For example, the first and second pulleys 58, 60 could have substantially the same diameters or the diameter of the first pulley could be substantially larger than the diameter of the second pulley.

A transfer shaft 64 of the drive assembly 16 operatively connects the second pulley 60 to the wheel 42 of the slider-crank assembly 14. As seen in FIG. 2, the transfer shaft 64 is supported by a pair of shaft supports 66. One of the shaft supports 66 is disposed adjacent the second pulley 60 and the other shaft support is disposed adjacent the wheel 42.

The platform assembly 18 is generally L-shaped and includes a generally vertical platform 70 and a generally horizontal platform 72. A pair of brackets 74 extends between the vertical platform 70 and horizontal platform 72 to reinforce the horizontal platform. As seen in FIG. 1, the horizontal platform 72 is sized and shaped for mounting the guide assembly 12, the slider-crank assembly 14, and the drive assembly 16 thereon. In one suitable embodiment, the vertical platform 70, horizontal platform 72, and brackets 74 are formed from metal plates. It is understood, however, that the platform assembly 18 can have any suitable configuration and be made from any suitable material.

Figure 6:
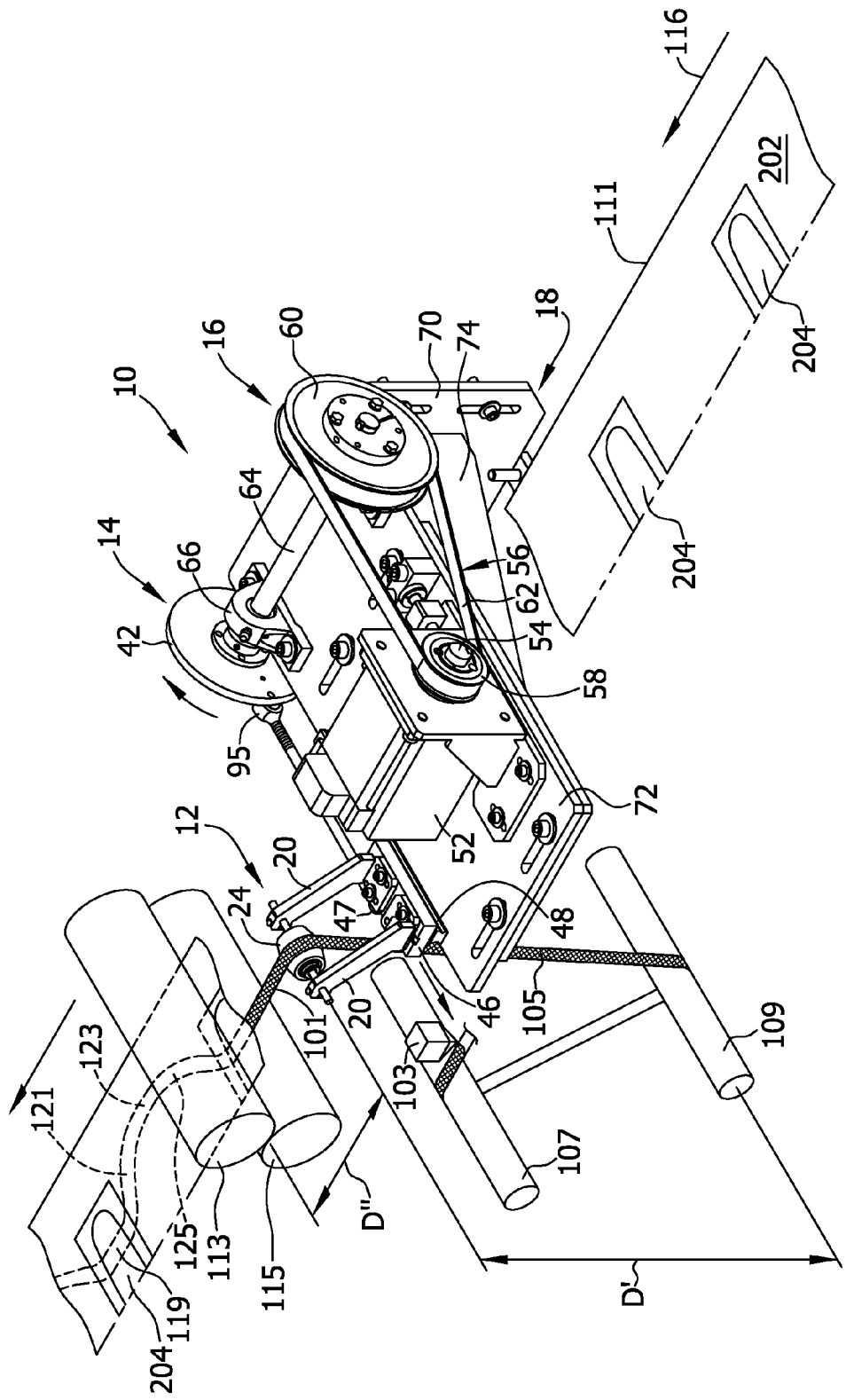
FIGS. 6-9 are sequential perspectives illustrating the apparatus applying a ribbon to a web moving at high line speeds.

In use, ribbon 101 is fed from a suitable ribbon source (not shown) past an adhesive applicator 103 where adhesive 105 is applied to one side of the ribbon (FIG. 6). In one suitable embodiment, the ribbon 101 is an elastic material suitable for use as leg elastics in an absorbent article. As an example, one suitable material for the ribbon 101 is a three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al. It is understood, however, that the ribbon 101 may be other materials including, but not limited to, wovens, films, foam/film laminates and combinations thereof without departing from the scope of this invention.

As seen in FIG. 6, the ribbon 101 is fed from the adhesive applicator 103 past first and second guide rollers 107, 109 to the roller 24 of the guide assembly 12. The ribbon 101 is fed to the roller 24 under tension which causes the ribbon to stretch. In one suitable embodiment, the ribbon 101 is under about 0.1 pound to about 1 pound per CD inch of tension. It is understood, however, that the tensional force applied to ribbon 101 can be different that disclosed herein.

With reference still to FIG. 6, the second guide roller 109 is spaced from the roller 24 of the guide assembly 12 by a distance D'. The distance D' is selected to facilitate proper alignment of the ribbon 101 as it is fed to the roller 24 and to inhibit twisting or bunching of the ribbon during movement of the roller relative to the second guide roller, which is stationary. In one suitable configuration, the distance between the second guide roller 109 and the roller 24 is approximately 10 times the width of the ribbon.

In the illustrated embodiment, the ribbon 101 is wrapped around approximately 130 degrees of the circumference of the roller 24. In other words, the ribbon 101 extends around about a third of the circumference of the roller 24 as it passes over the roller. It is understood that the ribbon can be wrapped around more or less of the roller 24 by changing the angle at which the ribbon is fed to the roller (i.e., the approach angle of the ribbon).

In the illustrated embodiment, the ribbon 101 is fed passed the roller 24 generally at the transverse center of the roller. As mentioned above, the roller 24 is a truncated prolate spheroid that tapers from its transverse center toward each of its edges. The shape of the roller 24 inhibits the ribbon 101 from sliding along the length of the roller. In other words, the shape of the roller 24 facilitates maintaining the ribbon 101 at the transverse center of the roller.

The roller 24 rotates about the shaft as the ribbon 101 is fed passed the roller. More specifically, the roller 24 is free to rotate relative to the shaft about the bearings 43 disposed between the roller and shaft.

As seen in FIG. 6, the ribbon 101 is fed past the roller 24 to a web 111 adjacent a pair of rollers 113, 115. A portion of the web 111, which is moving in a machine direction (indicated by arrow 116) over the apparatus 10, is cut away in FIGS. 6-9 to show the apparatus. It is contemplated that the web 111 could be fed beneath the apparatus 10 in other suitable embodiments.

Figure 10:
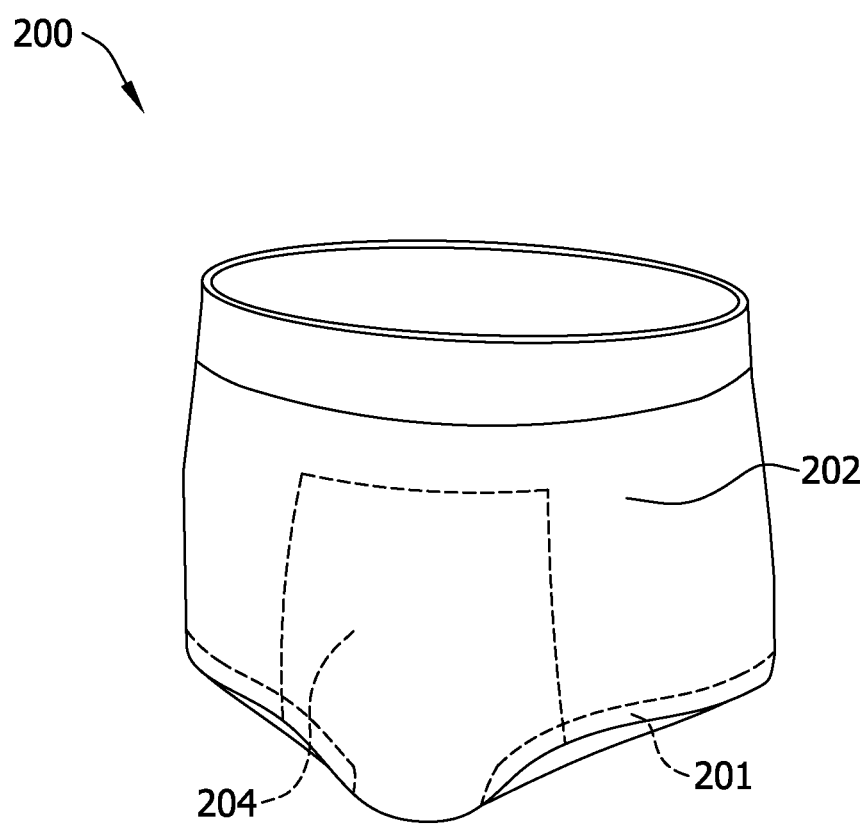
FIG. 10 is a perspective of one embodiment of an incontinence garment.

In the illustrated embodiment, the web 111 comprises a plurality of absorbent article assemblies arranged in a cross-machine direction. It is understood, however, that the absorbent article assemblies can be arranged in the machine direction instead of the cross-machine direction as seen in FIG. 6. More specifically, the illustrated web 111 comprises a continuous web of material suitable for use as an outer cover 202 of an absorbent article 200 and a plurality of spaced apart absorbent cores 204 attached to the web. In one suitable embodiment, the absorbent article 200 in the form of an incontinence garment as illustrated in FIG. 10 and described in more detail below. It is understood, that the web 101 can be any suitable material (e.g., material suitable for as an a bodyside liner) and intended for use in other articles including other types of absorbent articles (e.g., diapers, training pants).

With reference still to FIG. 6, the rollers 113, 115 collectively define a nip 117 through which the ribbon 101, the adhesive 105, and the web 111 pass to facilitate adherence of the ribbon onto the web. In one suitable embodiment, a distance D" between the roller 24 of the guide assembly 12 and the nip 117 is minimized to inhibit misalignment of the ribbon 101 relative to the web 111 before the ribbon is adhesively bonded to the web. Suitably, the distance D' between the roller 24 and the nip 117 is less than about 60 millimeters and suitable between about 50 millimeters and about 20 millimeters.

In one suitable embodiment, the web 111 is traveling at a high line speed. As used herein, high line speed refers to a line speed greater than about 600 feet per minute.

The alignment of the ribbon 101 relative to the web 111 is controlled using the apparatus described above. The apparatus 10 is capable of applying the ribbon 101 to the web 111 in a generally linear pattern (e.g., straight), a nonlinear pattern (e.g., curved), and a combination wherein portions of the ribbon are applied linearly and other portions of the ribbon are applied nonlinearly. In one suitable embodiment, the apparatus 10 is adapted to apply the ribbon 101 to the web 111 with significant curvature while the web is travel at high line speeds. As used herein, significant curvature means that the radius of curvature of the ribbon is greater than about 1 inch at least along one segment of its length. Suitably, at least a segment of the ribbon has a radius of curvature between about 3 inches and about 10 inches.

In the illustrated embodiment, the motor 52 of the drive assembly 16 rotationally drives the drive shaft 54 in a counterclockwise direction. The rate at which the motor rotates the drive shaft is variable and is used to control the rate at which the roller 24 and, more specifically, the guide assembly 12 reciprocates. It is understood that the motor 52 can drive the drive shaft at a constant rotational rate and in the clockwise direction. In the illustrated embodiment, the guide assembly 12 reciprocates along an axis of motion, which in the cross-machine direction (i.e., perpendicular to the machine direction). It is understood, however, that the guide assembly 12 can reciprocate at different orientations.

The guide assembly 12, which is attached to the slider, moves conjointly with the slider 64. Accordingly, the roller 24 follows the same motion profile as the slider 64. As mentioned, the roller 24 directs placement of the ribbon 101 onto the web 111. Thus, the operation of the motor 52 can be selectively controlled to control the placement pattern of the ribbon 101 onto the web 111. In the illustrated embodiment, for example, the motor 52 is paused (i.e., stopped) or slowed considerably in FIG. 6 such that the ribbon 101 is placed onto the web 111 in a generally straight line to form a first generally straight segment 119 of the ribbon.

The rotation rate of the drive shaft is then increased by the motor 52 to form a first curved portion 121 of the ribbon 101. During this increase in rotation rate, the drive shaft 54 of the drive assembly 16 causes the first pulley 58 of the belt and pulley subassembly 56 to rotate. The first pulley 58 drives the belt 62 and thereby the second pulley 60. Rotation of the second pulley 60 causes rotation of the wheel 42 of the slider-crank assembly 14 via the shaft 64 extending therebetween.

Figure 7:
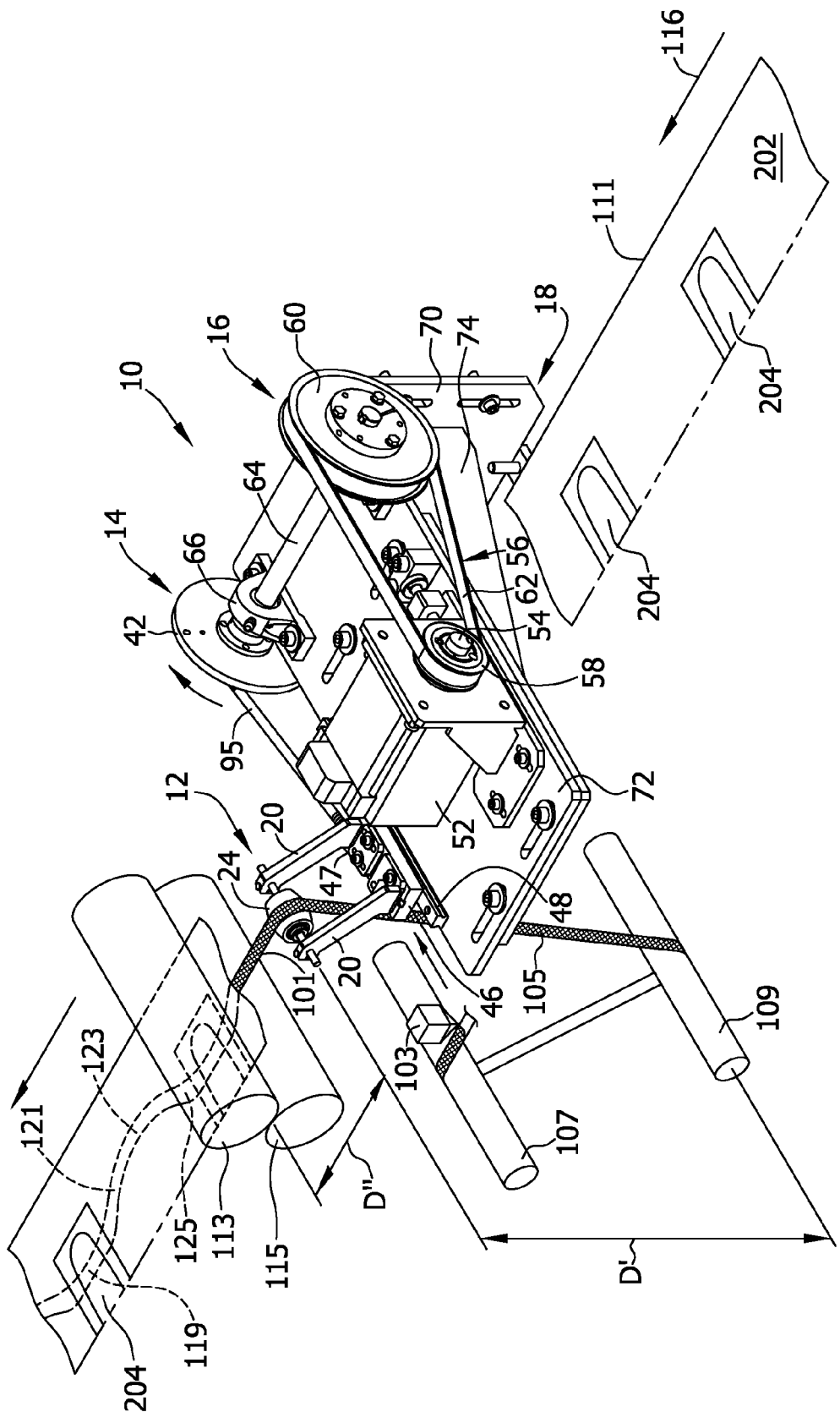

The position of the rod 44 on the wheel 42 dictates the relative position of the slider 46 and thus, the guide assembly 12. For example, in FIG. 6, the end 45 of the rod 44 attached to the wheel 42 is at an approximately 3 o'clock position, which results in the slider 64 and guide assembly 12 being in its left most position (as viewed in FIG. 6). As the wheel 42 rotates in a counterclockwise direction, the end 45 of the rod 44 moves conjointly with the wheel 42 towards a 12 o'clock position as seen in FIG. 7, which causes the slider 64 to move along the rail 48 toward the wheel (i.e., to the right as viewed in FIG. 7). The guide assembly 12, including the roller 24, moves with the slider 64 which directs the ribbon 101 onto the web 111 in a curved pattern.

Figure 8:
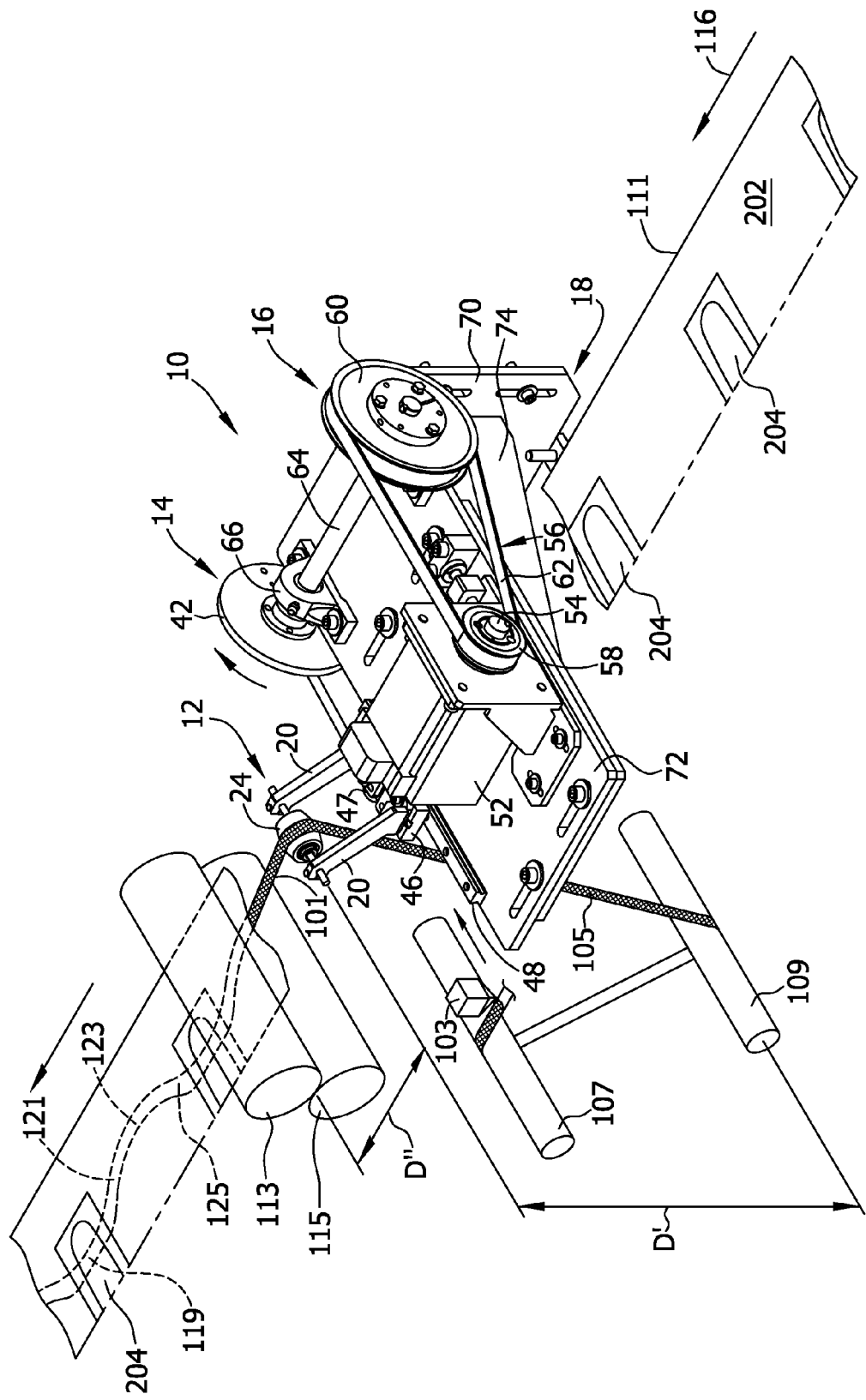

The slider 64 and thereby the guide assembly 12 continues to move towards the right as viewed in FIG. 7 until the end 45 of the rod 44 of the slider-crank assembly 16 reaches the 9 o'clock position, which is illustrated in FIG. 8. At this position, the rod 44, the slider 64, and guide assembly 12 are located in their right most position as viewed in FIG. 8. As a result, the roller 24 and thereby the ribbon 101 are also in their right most position as viewed in the Figures and the ribbon is attached to the web to form an apex 123 of the curved ribbon.

Figure 9:
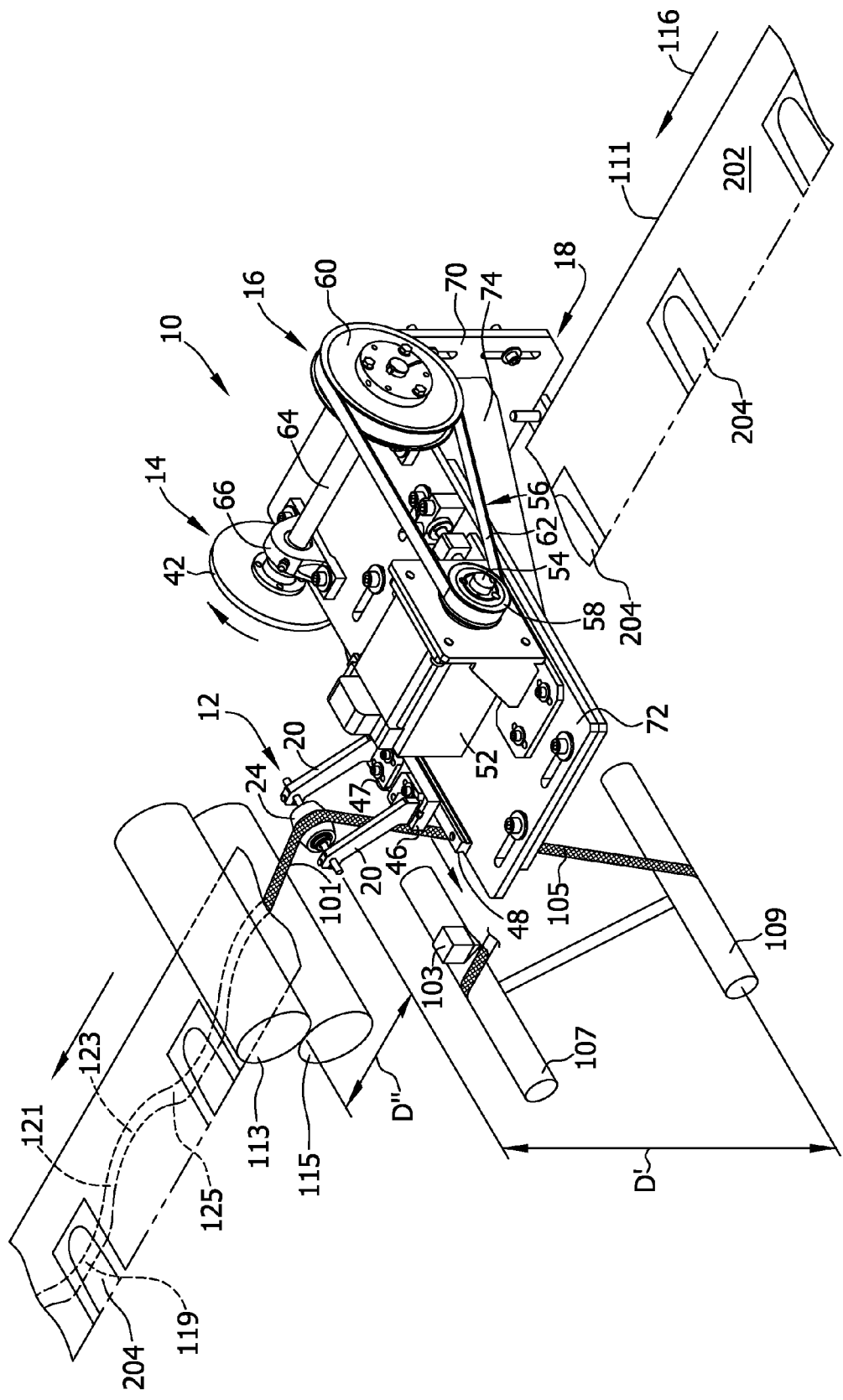

As the wheel 42 continues to rotate in the counterclockwise direction and the end 45 of the rod 44 is moved passed the 9 o'clock position, the slider 64 begins to be pushed by the rod in the opposite direction along the rail 48 (i.e., to the left as viewed in FIG. 8). FIG. 9 illustrates the wheel 42 continuing to rotate in the counterclockwise direction, the end 45 of the rod 44 at a generally 6 o'clock position, and slider 64 being moved along the rail 48 toward the left as viewed in FIG. 8. The slider 64 and guide assembly 12 continues to move towards the left until the end 45 of the rod 44 moves past the 9 o'clock position, which is illustrated in FIG. 6. This movement of the guide assembly 12 creates a second generally curved portion 125 in the ribbon 101 as it is applied to the web 111.

FIGS. 6-9 collectively illustrate one full revolution of the wheel 42 (i.e., 360 degrees of travel) of the slider-crank mechanism 14. Thus, the slider 64 reciprocates one full cycle per revolution. Thus, multiple revolutions results in an equal number of reciprocations of the slider 64. In the illustrated embodiment, the ribbon 101 is applied to the web 111 in a generally sinusoidal pattern. It is understood, however, that the patterns of the ribbon 101 on the web 111 can be different than those illustrated herein.

The range (i.e., the transverse displacement) of movement of the slider 64 along the rail 48 can be altered by changing the distance D between the center 50 of the wheel 42 and the end 45 of the rod 44 attached to the wheel. For example, the range of movement of the slider 64 can be reduced by reducing the distance D between the center 50 of the wheel 42 and the end 45 of the rod 44 attached to the wheel. Conversely, the range of movement of the slider 64 can be increased by increasing the distance D between the center 50 of the wheel 42 and the end 45 of the rod 44 attached to the wheel. The rate at which the slider 64 reciprocates along the rail 48 can be constant, increased, decreased, or stopped via the motor 52. As mentioned above, the guide assembly 12 moves conjointly with the slider 64. Thus, changes in the movement profiles of the slider 64 results in the same changes in the movement profile of the guide assembly 12.

One suitable embodiment of the incontinence garment 200 incorporating the web 111 having the ribbon 101 adhesively bonded thereto is illustrated in FIG. 10 in an assembled configuration. As seen therein, the garment 200 comprises the outer cover 202, the absorbent core 204 and leg elastics 201, which are defined by the ribbon 101. It is understood that the garment 200 can include numerous other components (e.g., a bodyside liner, fasteners) than those illustrated and described herein.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A method of applying a ribbon to a web, the method comprising:
   continuously feeding a web at a line speed of at least about 600 feet per minute in a machine direction; and
   guiding a ribbon to the web using a reciprocating guide roller, the ribbon being applied by the guide roller in a nonlinear pattern such that at least a portion of the ribbon has a radius of curvature between about 3 inches and about 10 inches.

2. The method as set forth in claim 1 further comprising tensioning the ribbon prior to applying the ribbon to the web.

3. The method as set forth in claim 1 further comprising applying adhesive to the ribbon prior to applying the ribbon to the web.

4. The method as set forth in claim 1 wherein feeding a web comprises feeding a plurality of connected absorbent article assemblies.

5. The method as set forth in claim 4 wherein the absorbent article assemblies are arranged in a cross-machine direction.

6. The method as set forth in claim 1 further comprising feeding the web and the ribbon through a nip defined by a pair of rollers.

7. The method as set forth in claim 1 further comprising reciprocating the guide roller along an axis of motion, the axis of motion being generally perpendicular to the machine direction.

8. Apparatus for applying ribbon in a nonlinear pattern to a web, the apparatus comprising:
   a guide assembly including a roller adapted to rotate about an axis of rotation to guide the ribbon onto the web as the web is moving in a first direction; and
   a reciprocating device for moving at least the roller of the guide assembly back and forth along an axis of motion, the axis of motion being other than parallel to the first direction, the reciprocating device being capable of moving at least the roller back and forth at variable speeds, wherein the guide assembly further includes at least one support arm interconnecting the roller to the reciprocating device, the at least one support arm being oriented other than parallel to the axis of rotation.

9. The apparatus as set forth in claim 8 wherein the axis of motion is generally perpendicular to the first direction.

10. The apparatus as set forth in claim 8 wherein the reciprocating device comprises a rail and slider mounted on the rail, the slider being capable of sliding relative to the rail, the guide assembly being coupled to the slider.

11. The apparatus as set forth in claim 8 wherein the roller is generally a truncated prolate spheroid.

12. The apparatus as set forth in claim 8 wherein the guide assembly further includes a shaft supported by the at least one support arm, the roller being rotatably mounted on the shaft.

13. The apparatus as set forth in claim 8 wherein the reciprocating device comprises a slider-crank assembly.

14. The apparatus as set forth in claim 13 further comprising a drive assembly operatively connected to the slider-crank assembly.

15. The apparatus as set forth in claim 8 wherein the roller is mounted on a shaft, the roller being free to rotate relative to the shaft.

16. The apparatus as set forth in claim 8, wherein the at least one support arm comprises a pair of support arms oriented perpendicular to the axis of rotation, wherein the roller is disposed between the pair of support arms.

17. Apparatus for applying ribbon in a nonlinear pattern to a web, the apparatus comprising:
   a web feeding device configured to continuously feed the web in a first direction at a line speed of at least about 600 feet per minute;
   a guide assembly including a roller adapted to guide the ribbon onto the web as the web is being continuously fed in the first direction at the line speed; and
   a slider-crank assembly operatively connected to guide assembly to impart reciprocating motion on at least the roller of the guide assembly so that the roller can be moved back and forth relative to the web as it guides the ribbon onto the web.

18. The apparatus as set forth in claim 17 wherein the slider-crank assembly comprises a wheel, a rod secured at one end to the wheel, and a slider secured to the opposite end of the rod, the guide assembly being mounted on the slider, wherein rotation of wheel is transferred by the rod to slider as reciprocating motion.

19. The apparatus as set forth in claim 18 wherein the wheel is generally circular.

20. The apparatus as set forth in claim 18 wherein the end of the rod is releasably attachable to the wheel at a plurality of locations.

21. The apparatus as set forth in claim 20 further comprising a drive assembly for driving the slider-crank assembly.

22. The apparatus as set forth in claim 21 wherein the drive assembly comprises a variable speed motor operatively connected to the slider-crank assembly.

23. The apparatus as set forth in claim 22 wherein the drive assembly further comprises a belt and pulley subassembly operatively connecting the motor to the slider-crank assembly.

24. The apparatus as set forth in claim 22 wherein the motor is adapted to rotate in both the clockwise and counterclockwise directions.

25. The apparatus as set forth in claim 17, wherein the roller is adapted to rotate about an axis of rotation, and the guide assembly further includes at least one support arm interconnecting the roller to the reciprocating device, the at least one support arm being oriented other than parallel to the axis of rotation.

\* \* \* \* \*